United States Patent [19]
Perrier et al.

[11] Patent Number: 6,132,750
[45] Date of Patent: Oct. 17, 2000

[54] PARTICLES OF CROSS-LINKED PROTEINS AND POLYSACCHARIDES WITH HYDROXAMIC GROUPS FOR CHELATING METALS AND THEIR USES NOTABLY IN COSMETICS

[75] Inventors: Eric Perrier, Les Cotes d'Arey; Chantal Buffevant, Millery; Isabelle Bonnet, Lyons; Marie-Christine Levy, Reims, all of France

[73] Assignee: Coletica, France

[21] Appl. No.: 09/108,670

[22] Filed: Jul. 1, 1998

[30] Foreign Application Priority Data

Apr. 14, 1998 [FR] France .................................. 98 04611

[51] Int. Cl.$^7$ ..................................................... A61K 7/00
[52] U.S. Cl. .......................... 424/418; 424/401; 424/449; 424/489; 514/963; 264/4.3; 264/4.32; 264/4.7; 428/402.24
[58] Field of Search ..................................... 424/401, 418, 424/489, 490, 491, 492, 493, 494, 495, 499; 514/963; 264/4.1, 4.3, 4.32, 4.7; 428/402.24

[56] References Cited

U.S. PATENT DOCUMENTS 5,395,620  3/1995  Huc et al. ............................... 424/499

FOREIGN PATENT DOCUMENTS 0611326  10/1992  European Pat. Off. .
0630287  10/1993  European Pat. Off. .

OTHER PUBLICATIONS

Hettler D. et al.—"Polyhydroxamic Microcapsules Prepared From Proteins: A Novel Type Of Chelating Microcapsules" Journal of Microencapsulation, vol. II, No. 2, 1 mars 1994, pp. 213–224.

Levy, M.C. et al.—"Polyhydroxamic Serum Albumin Microcapsules: Preparation And Chelating Properties"— International Journal of Pharmaceutics, vol. 69, 1991, pp. R1–R4.

Levy, M.C. et al.—"Mixed–Walled Microcapsules Made Of Cross–Linked Proteins and Polysaccharides: Preparation And Properties"—Journal of Microencapsulation, vol. 8, No. 3, 1 juillet 1991, pp. 335–347.

Rongved Pal et al.—"Cross–Linked, Degradable Starch Microspheres As Carriers Of Parmagnetic Contrast Agents For Magnetic Resonance Imaging: Synthesis, Degradation, And Relaxation Properties"—Carbohydrate Research, vol. 214, 1991, pp. 325–330

J. Med. Chem. 1981, 24, 1263–1266, Margel, "A Novel Approach for Heavy Metal Poisoning Treatment, a Model, Mercury Poisoning by means of Chelating Microspheres: Hemoperfusion and Oral Administration".

J. Nuclear Med. 22, 623–626, 1981, Hnatovitch et al., "Albumin Microspheres Labeled with Ga–67 by Chelation: Concise Communication".

Magnetic Resonance Quarterly, 6, 65–84, 1990, Lauffer, "Magnetic Resonance Contrase Media: Principles and Progress".

Carbohydrate Res. 214, 325–330, 1991, Rongved et al., "Cross–linked, degradable starch microspheres as carriers of paramagnetic contrast agents for magnetic resonance imaging: Synthesis, degradation, and relaxation properties".

J. Microencapsulation, 1994, vol. 11, No. 2, pp. 213–224, Hettler et al., "Polyhydroxamic microcapsules prepared from proteins: a novel type of chelating microcapsules".

*Primary Examiner*—Jose' G. Dees
*Assistant Examiner*—Michael A. Williamson
*Attorney, Agent, or Firm*—Bierman, Muserlian and Lucas

[57] ABSTRACT

The invention relates to small sized particles.

These particles comprise at least on the surface thereof a wall composed of a mixture of at least one protein and at least one polysaccharide which are cross-linked, preferably by interfacial cross-linking with a polyfunctional acylating agent which forms at least amide and ester bonds, and optionally anhydride bonds with amine, hydroxyl or carboxyl functions of the protein and of the polysaccharide, and which comprise hydroxamic groups on the surface thereof for chelating metal ions.

These particles can be used in cosmetics or in pharmacy notably for the chelation or release of metal ions.

45 Claims, No Drawings

PARTICLES OF CROSS-LINKED PROTEINS AND POLYSACCHARIDES WITH HYDROXAMIC GROUPS FOR CHELATING METALS AND THEIR USES NOTABLY IN COSMETICS

The present invention essentially relates to small-sized particles having a mixed wall of cross-linked proteins and cross-linked polysaccharides, which particles comprise hydroxamic groups on the surface thereof, which chelate metal ions, their method of preparation and their various uses, notably in cosmetics, pharmacy and agro-foodstuffs.

Within the context of the present invention and claims, the term "small-sized particle(s)" signifies both microparticles and nanoparticles and the terms "microparticles" or "nanoparticles" relate to microspheres or nanospheres as well as microcapsules or nanocapsules.

On the other hand, the terms "microspheres" or "nanospheres" cover particles comprising an essentially uniform structure in the whole of their mass, whilst the terms "microcapsules" or "nanocapsules" cover particles comprising a cross-linked wall which surrounds an internal nucleus or space filled with a solid, gelified, liquid or gaseous medium.

Within the context of the present invention, these small-sized particles comprise at least on the surface thereof a wall composed of a mixture of at least one protein and at least one polysaccharide which are cross-linked, preferably by interfacial cross-linking with a polyfunctional acylating interfacial cross-linking agent, according to an interfacial cross-linking reaction well-known to the person skilled in the art and which shall be described in greater detail farther on.

Within the context of the invention, these small-sized particles further comprise on the surface thereof multiple hydroxamic groups obtained by a reaction of the small-sized particles with cross-linked surface which comprise a certain number of ester bonds and optionally anhydride bonds, with hydroxylamine in a basic medium in thus enabling these small-sized particles to be given a capacity to chelate metal ions such as shall be described further on in greater detail.

STATE OF THE PRIOR ART

The finer understanding of biological mechanisms very frequently enables one to demonstrate the preponderant role of metal ions in chemical reactions, physical reactions or biological reactions.

According to the case, these metal ions can be useful, even essential (trace elements) or can induce positive reactions against organisms, or can be useless, even extremely toxic (heavy metals) and thus induce oxidation reactions, necrosis, and cell death.

The capture and removal of the toxic effect of these metal ions, such as the provision of certain metal ions which possess a positive effect prove to be intense routes of research: the multiple needs in the fields of agro-foodstuffs, in the treatment of used waters, in the medical and biomedical fields, as well as in the cosmetics field do in fact bring together the research in directions which are common to the whole of these fields, without major distinctions.

One greatly explored route calls for the development of novel chemical entities which enable chelating metal ions more and more efficiently (EDTA and its derivatives, HEDTA and its derivatives, DTPA and its derivatives, 2-furyldioxime, etc . . . ). The principal problem linked to the use of these substances concerns the soluble character of these chelating agents, which can only be very arduously separated from the medium in which they were placed. Thus, it cannot be envisaged to easily remove a metal ion from an aqueous solution with the aid of a chelating agent which itself is soluble in aqueous solution, it being not always possible for the methods of separation conventionally used (filtration, decantation, centrifugation, . . . ) to be applied.

Another route which enables solving the problem of separation consists in using solid particles which possess capacities of trapping metal ions.

Conventionally, ion exchange resins are usable, but these, prepared from polystyrene or formophenol polymers, are not biodegradable and are not biocompatible, and can give off highly cytotoxic side-products or monomers (formol, phenol, styrene..) which are often not compatible with the applications linked to the living being (applications in life sciences, diagnostics, agro-foodstuff uses, pharmaceuticals or cosmetics . . . ).

Medical applications were envisaged by Margel (J. Med. Chem., 24, 1263–1266, 1981) for the treatment of poisoning with heavy metals by chelating microspheres, and applications in medical imaging were proposed by Hnatovitch et al. (J. Nuclear Med., 22, 623–626, 1981), Lauffer (Magnetic Resonance Quarterly, 6, 65–84, 1990) and Rongved et al. (Carbohydrate Res., 214, 325–330, 1991) for microspheres loaded with elements which are possible to follow in the organism.

On the other hand, it is known from the document EP-0 611 326 B1 of the Applicant about the preparation of nanoparticles or nanocapsules from proteins cross-linked by interfacial cross-linking which encapsulate an active principle in order to enable, in a surprising manner, a slow-release of this active principle. It is also known from the prior art document of the Applicant EP-0 630 287 B1 about a method of preparing microcapsules or microspheres having walls of polysaccharide by interfacial cross-linking; it being possible for them to contain a hydrosoluble, hydrodispersible, insoluble or liposoluble active substance. The Applicant has even described, in the document U.S. Pat. No. 5,395,620, the preparation of biodegradable microcapsules having mixed walls of cross-linked atelocollagen and polyholosides for encapsulating cosmetic, pharmaceutical or agro-foodstuff active principles.

In the prior art, the article published by D. Hettler, M. C. Andry and M. C. Levy, one of the co-inventors of the present invention, entitled "Polyhydroxamic microcapsules prepared from proteins: A novel type of chelating microcapsules", appearing in J. Microencapsulation, 1994, volume 11, No. 2, pages 213–224, describes the preparation of microcapsules from proteins constituted by human serum albumin (abbreviated to HSA), fibrinogen of bovine origin and ovalbumin, obtained by a method of interfacial cross-linking and treated with hydroxylamine in an alkaline medium so as to rupture the ester and anhydride bonds of the wall of the microcapsules in order to bind hydroxamic groups thereon onto the wall or membrane, the binding of the hydroxamic groups enabling the microcapsules to acquire the property of binding metal ions and especially iron.

However, it is shown in this document in the results part and the discussion part on page 216 to page 223 that the microcapsules suffer from a significant decrease in density which renders their sedimentation much more difficult (last line of page 216 and first line under the table 1 of page 217).

On the other hand, the microcapsules are thus much more sensitive to the enzymatic degradation by trypsin wherein a degradation in five minutes is obtained in contrast to a degradation time of twenty minutes for HCA microcapsules and of a complete resistance to trypsin of the microcapsules of ovalbumin and fibrinogen which were non-treated with hydroxylamine.

On the other hand, in tests with greater quantities, of the industrial type, the present inventors have noted a complete destruction of the microcapsules during treatment with hydroxylamine in an alkaline medium which destroys the practical interest, especially on an industrial scale of this method.

Within the context of these industrial type tests, the proportion of the proteins cannot in general be greater than about 5% by weight, largely due to reasons of viscosity, and this does not enable one to prepare cross-linked particles having walls resistant to hydroxylaminolysis.

AIMS OF THE INVENTION

The principal aim of the present invention is to solve the novel technical problem consisting of providing novel chemical entities constituted by biocompatible, biodegradable particles, which are capable of chelating metal ions and of being isolated easily from a reaction medium or from a chelation medium in which said ions are present.

Another principal aim of the present invention is to solve the novel technical problems which consist in providing biocompatible, biodegradable, small-sized particles capable of chelating metal ions easily isolable from the reaction medium, which should be extremely stable in aqueous media, which should not be prepared from materials which are susceptible to be forbidden in the various applications envisaged, and which must be able to be prepared industrially in very good yield in order to enable the preparation of significant quantities.

Another principal aim of the present invention is to solve the novel technical problem which consists in providing particles having a very good capacity to chelate metal ions and which are mechanically and/or biologically resistant, especially as regards an enzymatic lysis.

Another principle aim of the present invention is to solve the novel technical problem consisting of providing particles initially loaded with various chelated metal ions, radioactive or non-radioactive metal ions, which are usable in a given medium in order to exert a specific role or a specific activity, directly or by release of the chelated metal ions.

Another principle aim of the present invention is to solve the technical problems set forth above without significantly increasing the cost of preparation of such particles, while at the same time enabling preparing at will either capsules, or spheres, on the other hand equally of micrometric or nanometric dimensions with an ease of regulation of their mechanical resistance capacity and/or by a biological resistance capacity especially as regards enzymatic lysis.

SUMMARY OF THE INVENTION

In order to solve these novel technical problems, it has occurred to the present inventors that the method described above by at least one of the co-inventors of the present invention, namely that described in J. Microencapsulation 11, 213224, 1994, uses proteins which are forbidden for certain applications, namely human albumin, which is forbidden in cosmetology, or proteins which are heavily regulated for other applications, such as proteins derived from bovines, ovines, caprines, in cosmetology and in pharmacy, and also due to the high cost such as fibrinogen, which limits the fields of application of the products originating from this technique.

The inventors have therefore sought to use proteins which are wide spread in nature, which are non-regulated, and which should be usable in methods and industrial applications.

Thus, various proteins collagen, including marine collagen, gelatine, including marine gelatine, soya proteins, pea proteins, lupin proteins, bean proteins, etc . . . ) have been used in following the methods described in the patents which have furthermore been filed by certain co-inventors of the present invention, especially the document U.S. Pat. No. 5,395,620, but the results were negative since during the treatment with hydroxylamine in alkaline medium, the microspheres prepared were irreversibly lysed without it being possible to control the intensity of this lysis, which leads to a massive destruction of the microspheres, as well as to industrial yields of nearly nothing which do not enable envisaging the use of these microspheres in the numerous applications envisaged by the present inventors.

Similarly, when particles of polysaccharides are used which are cross-linked by an acid dichloride, and which are treated with alkaline hydroxylamine, an immediate destruction is observed of the particles due to a hydroxylaminolysis of the ester bonds.

Faced with this novel technical problem, the present inventors have discovered in a totally unexpected way that if a solution containing a mixture of at least one protein and at least one polysaccharide is used for preparing the particles, the particles obtained, having mixed walls of cross-linked protein and polysaccharide, are capable of resisting the hydroxylaminolysis treatment and of chelating metal ions.

Thus, according to a first aspect, the invention provides small-sized particles which comprise, at least on the surface thereof, a wall composed of a mixture of at least one protein and at least one polysaccharide which are cross-linked, preferably by interfacial cross-linking with a polyfunctional acylating cross-linking agent which forms at least amide and ester bonds and optionally anhydride bonds, with amine, hydroxyl or carboxyl functions of the protein and of the polysaccharide, and which comprises hydroxamic groups on the surface thereof for chelating metal ions.

Advantageously, the hydroxamic groups are bound onto the surface by reaction of the particles, cross-linked by the above-mentioned cross-linking agent, with hydroxylamine in an alkaline medium according to the procedure described in Hettler et al. mentioned above and given in detail further on.

Without intending to be linked or limited to any theory, it would seem that during the treatment of the particles having mixed walls of cross-linked protein and polysaccharide with hydroxylamine in alkaline medium, the bonds in these particles are less sensitive to hydroxylaminolysis than in the case of the particles prepared from cross-linked proteins alone, or from cross-linked polysaccharides alone. On the other hand, within the context of the cross-inking of a mixture of proteins and polysaccharides, with a polyfunctional acylating interfacial cross-linking agent such as an acid dihalide or an acid dianhydride, the hydroxyl functions and optionally the carboxyl functions of the polysaccharides participate in a cross-linking reaction with the polyfunctional interfacial cross-linking agent, as was described in the prior document of the applicant U.S. Pat. No. 5,395,620. It would seem that the resistance to hydroxylaminolysis of the particles having mixed walls of cross-linked proteins and polysaccharides should be linked to the formation of an association complex in the initial aqueous phase between the polysaccharide and the protein. This complex would give, after interfacial cross-linking, a membrane which is strengthened by virtue of the multiple covalent bonds which would be established between the two biopolymers via the interfacial cross-linking agent. The hydroxylaminolysis would give rise to hydroxamates from a certain number of ester bonds and optionally anhydride bonds. However, sufficient intact bonds protected in the complex would remain after treatment in order to assure the entirety of the membrane.

The polysaccharides which are particularly advantageous in enabling a binding of the hydroxamic groups without significantly degrading the structure of the cross-linked particles are xanthan, guar, carobe, karaya gums, gum Arabic, alginates, agars, carrageenins, scleroglucans, gluco- and galacto-mannans, the arabinogalactans, pectins, glycosaminoglycans, pentosans, dextrans, chitosan and derivatives thereof, hydrosoluble and hydrodispersible derivatives of starch or of cellulose such as alkyl ethers, hydroxyalkyl ethers or carboxyalkyl ethers of starch or alkyl ethers, hydroxyalkyl ethers or carboxyalkyl ethers of cellulose, such as hydroxypropyl celluloses, carboxymethyl celluloses.

As mentioned before, these small-sized particles bearing hydroxamic groups are generally prepared in two distinct steps, a first step which consists in preparing small-sized particles, for example micro- or nanospheres or micro- or nanocapsules, by interfacial polycondensation between a mixture of protein(s) and polysaccharide(s) on the one hand, and a polyfunctional acylating cross-linking agent on the other, particularly a diacid halide, preferably a diacid chloride, at the interface of the phases of an emulsion, in particular of the "water-in-oil" or "oil-in-water" type, in thus obtaining small-sized particles having at least the wall on the surface thereof cross-linked, as reaction product.

In a second step, these small-sized particles are allowed to react with hydroxylamine in alkaline medium in order to introduce onto the surface of these small-sized particles a plurality of hydroxamic groups resulting from the rupture of at least the corresponding ester bonds and optionally the corresponding anhydride bonds, formed from said cross-linking which enables binding said hydroxamic groups onto the functions thus released.

As regards the interfacial cross-linking reaction, this is well-known to the person skilled in the art.

As regards the mixtures of proteins and polysaccharides, the reaction can be used which is described in the preceding patent of the Applicant, U.S. Pat. No. 5,395,620, which enables one to obtain microcapsules or microparticles.

On the other hand, the interfacial cross-linking reaction described in the preceding document of the applicant EP-0, 630,287 B1 can also be used, which enables obtaining microcapsules or microspheres of polysaccharide by interfacial cross-linking.

Particles of nanometric size can also be obtained by using the method described in the preceding document of the applicant EP-0 611 326 B1.

The interfacial cross-linking method described in the document FR-A-9708968, which is not published as to this day, can also be used for the preparation of cross-linked small-sized particles which act as starting material for the above-mentioned second step of binding of hydroxamic functions, and which are resistant to this reaction.

The reaction conditions described in the document of Hettler, M. C. Andry and M. C. Levy in J. Microencapsulation, 1994, volume 11, No. 2, pages 213–224, mentioned above which is herein incorporated as a reference, can be used.

In this context, the method generally comprises placing the cross-linked small-sized particles obtained after the first step according to a cross-linking method such as described above, in suspension in water, in an alcohol, or in a mixture thereof, then introducing a concentrated hydroxylamine, for example at the concentration of 3M, with stirring, at ambient temperature, and then rendering the solution alkaline by the addition of a base such as sodium hydroxide for example, for example by the addition of concentrated NaOH such as 3.5 M ; the whole is left to stir for a period of time sufficient to enable the opening of at least the ester bonds and optionally the anhydride bonds resulting from the cross-linking, as described in the Hettler et al. Document, with the formation of hydroxamate groups of the type:

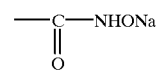

as described in this document.

The duration of the reaction is variable but may typically be between 15 and 30 minutes.

The hydroxylamine may also be used in the form of a salt such as a hydrochloride, phosphate, sulphate, which are available commercially, notably from Sigma, France. At the end of the reaction, various washings may be carried out until a roughly neutral pH is obtained.

On the other hand, according to another embodiment, an esterification step may be carried out before carrying out the grafting of the hydroxamic group onto the small-sized particles, as is also described in the preceding document of Hettler et al. (FIGS. 1c and 1d, page 214).

In this case, the esterification can be carried out as described in Hettler et al. in using an alcohol such as ethanol or benzyl alcohol, and 1-ethyl-3-(dimethylaminopropyl) carbodiimide HCl (abbreviated to EDCI) as described in the Hettler et al. document. This esterification enables increasing the number of hydroxamic groups formed after the hydroxylaminolysis step as shown in FIG. 1d, page 214 of Hettler et al.

The relative proportion of hydroxylamine (used in its commercial hydrochloride form) can vary within large limits and will generally be between 10 and 400 g per kilogram of wet particles to be treated, and more preferably between 30 and 200 g/Kg, the pH being adjusted by a strong base, preferably sodium hydroxide, to values between 9 and 13.5, more preferably between 9.5 and 13.

Within the context of the invention, small-sized particles such as micro- or nanospheres, or micro- or nanocapsules are obtained, which possess a large portion of hydroxamic groups, and which are characterised by the capacity of these particles to trap metal ions which shall be demonstrated in what follows of the present document.

As regards the proteins, any protein may be used without limitation. However, for certain preferred industrial applications, such as the cosmetic, pharmaceutical or agro-foodstuffs industry, it will be preferable to use a protein of non-regulated use, in particular one obtained industrially, such as, for example, collagen or atelocollagen, including marine collagen and marine atelocollagen, moderate hydrolysates of collagen, including marine collagen hydrolysates, gelatines including marine gelatines, or a plant protein such as, for example, plant proteins extracted from leguminous or proteagenous plants, in particular the following plants: lupin (genus Lupinus), soya (genus Glycine), pea (genus Pisum), chick pea (genus Cicer), lucerne (genus Medicago), bean (genus Vicea), lentil (genus Lens), bean (genus Phaseolus), sesame (genus Sesamum), rape (genus Brassica), or sunflower (genus Elientus), or even cereals such as, for example, wheat, maize, barley, malt, oats.

These plant proteins can be used in the form of a powdery preparation such as flowers, concentrates, isolates or liquid preparations such as soya milks.

The inventors have studied the chelation kinetics (maximum at 30 minutes of contact, and then stable), as well as the metal ions which are susceptible in being trapped by these small-sized chelating particles prepared as described above. The inventors have demonstrated that calcium, iron (II or III), copper (I or II), chromium, nickel, cobalt, mercury, zinc, silver, aluminium, cadmium, magnesium, lead, arsenic, silicon, selenium, germanium, gadolinium, manganese, metal ions of radioactive metals or of radioactive isotopes of metals, were able to be trapped onto the chelating particles of the invention. The radioactive metals can be selected for example from the radioactive isotopes of technetium (Tc 99 m), indium (In 111, In 113m), gold (Au 198), ruthenium (Ru 103), cobalt (Co 57), chromium (Cr 51), gadolinium (Gd 153), without limitation. The inventors have also demonstrated that this trapping is not linked to an adsorption of the metal ions onto the membrane of the spheres, since the trapped metal ions are bound in a totally stable manner and that no desorption is detectable with time, but to the formation of stable chelates which employ the hydroxamic groups.

The inventors have also demonstrated that this chelation was, under certain If conditions of pH, demonstrated by the inventors, to be entirely reversible, and this enables envisaging recycling these chelating microspheres and their rational use in numerous industrial applications.

According to another embodiment, the above-mentioned particle is initially loaded with chelated metal ions, and is usable in a given medium to exert a specific role or activity, directly or by release of the chelated metal ions, these ions being preferably selected from iron (II or III), copper (I or II), calcium, selenium, zinc, silver, silicon, germanium, magnesium, manganese.

According to another embodiment, the above-mentioned particle is initially loaded with metal ions of a radioactive metal or of a radioactive isotope of a metal, or even with a metal ion of a paramagnetic metal such as iron, manganese, gadolinium, and their alloys, said particle thus becoming detectable by imaging techniques, notably by scintigraphy or NMR imaging.

Thus, according to a second aspect, the present invention relates also to the use of small-sized particles described above, which comprise hydroxamic groups on the surface thereof for chelating metal ions, in particular, this use can be carried out for the preparation of cosmetic ingredients, cosmetic compositions, pharmaceutical compositions, or agro-foodstuff compositions or compositions for the treatment of liquids, in particular water.

The envisaged applications are the following:
the decontamination of biological materials or media such as blood, plasma, biological extracts, milk, etc., for the decontamination of water and industrial liquids, for the decontamination of oily preparations such as essential oils, for the decontamination of solvents, of silicones, or of complex organic media, of metals, in particular heavy metals such as lead, copper, iron, nickel, arsenic, mercury, chromium, or of traces of aluminium, or for the decontamination of any radioactive metal or radioactive isotope of metals, in thus enabling removing said metal ions, and for example "decontaminating" by this technique such media or liquids containing metals such as copper, iron, aluminium, lead, nickel, arsenic, mercury, chromium, compounds the content of which must be very rigorously controlled before putting substances on the market which may contain them, notably through being derived from preparation methods, for example by the use of catalysts, or being present as non-desired contaminants, for example pollutants.

trapping calcium and magnesium for treating water hardness.

trapping iron (but also copper and manganese), which is in particular a powerful inducer of oxidation reactions, radical reactions, which may induce browning, oxidation and degradation of noble substances (industrial applications and agro-foodstuff applications), but which may induce phenomena of oxidative stress, sunburn, cell degradation and cell death through the radical degradation of phospholipids (cosmetic and pharmaceutical applications, for uses in preparations enabling protecting the skin, both short term and long term, and photo-induced lesions). Rancidity inhibiting effects, stabilising effects of oxidation of oxidisable substances (vitamins for example) and UV-protecting effects are therefore claimed.

a model which enables demonstrating the effect of the products of the invention, i.e. particles, upon the photo-protecting power, has been developed in noting that the depolymerisation (radical cleavage) of hyaluronic acid (a natural polymer present in human skin and responsible for its firmness), observed in the presence of traces of iron, was accelerated by agents which are conventionally used for trapping iron (lactoferrin, transferrin, EDTA . . . ), whilst it is strongly checked by the products of the invention.

a use of the above-mentioned particles in cosmetic and dermo-pharmaceutical applications for the protecting property, including photo-protecting property, of the material of the dermis, inhibiting the effects of photo-induced ageing of cutaneous structures calcium trapping: enzymatic cofactor of a large number of enzymes including proteases, the chelation of calcium enables inhibiting certain enzymatic activities, including collagenase activities, involved in the degradation of the skin support tissues, and the intrinsic or photo-induced ageing of the skin tissues. A modulation of the collagenase activity is thus obtained.

copper trapping or release: copper is an enzymatic cofactor of a large number of enzymes (ceruleoplasmin, ferroxidase, cytochrome C oxidase, superoxide dismutase, ascorbate oxidase, tyrosinase, dopa beta hydroxylase, mono amine oxidase, . . . ). Chelating it enables inhibiting certain enzymatic activities including tyrosinase activities, involved in the uncontrolled pigmentation of the skin tissues under the action of UV (brown marks), or ascorbate oxidase activities which accelerate the decomposition of vitamin C. On the contrary, it is also possible to provide copper in a form which is complexed to the chelating microspheres of the invention, so as to stimulate the enzymatic activities such as that of mono amine oxidase, an essential enzyme during the cross-linking of the elastin fibres within the cutaneous architecture. Furthermore, various metal chelates of polyhydroxamic polymers can themselves exert a catalytic activity. Thus, for example, the copper $Cu^{2+}$ chelates of polymers of poly(acrylhydroxyamic) types have catalase properties: they catalyse the decomposition of hydrogen peroxide as described by Nozawa et al., Makromol.

Chem. 112, 73–83, 1968, and this renders them particularly interesting for cosmetic applications.

the copper chelated onto the hydroxamic functions also enables:

stimulating the formation of melanin (Kaneko et al., J. Polym. Sci. Macromol. Rev. 16, 397–522, 1981), and this enables envisaging its use in cosmetic formulations of the tanning activating type;

obtaining anti-inflammatory and anti-ulcer activities (Sorenson, J. Med. Chem. 19, 135–148, 1976), and this enables envisaging there use in applications of the anti-chemical or actinic bum type.

the provision of copper, selenium, zinc in the form of loaded chelating microspheres, can enable a better anti-radical defence of the skin, whilst at the same time activating its immune functions.

the use of silver: silver possesses very important bactericidal activities but is little used in cosmetics since its salts are difficult to manipulate. By chelating the silver ion onto the chelating microspheres, and by using the result obtained, it is possible to obtain intensely bactericidal and fungicidal properties, which are usable in cosmetics and dermatology, without the silver ions being in contact and being absorbed by the skin, and consequently without any risk of cutaneous intolerance.

the trapping of nickel and cobalt: these two agents are powerful allergens which can induce severe dermatoses. The introduction of chelating microspheres into formulations for topical use can enable reducing the problems linked to the accidental presence (pollution, etc . . . ) of one or the other of these two ingredients on the skin.

the delivery of silicon and/or germanium blocked onto the chelating microspheres, for applications via the topical route: these two ions have capital properties in cosmetics and the former has a role in the construction and the framework of the dermis.

the delivery of iron blocked onto the chelating microspheres, for the preparation of a pharmaceutical composition for an oral supplementation of iron, so as to diminish the toxicity usually brought about by iron used in the free state, in therapeutic applications in animals and preferably in man.

the blocking of any metal ion of a radioactive metal or of a radioactive isotope of a metal onto the chelating particles, and the applications of these microspheres in diagnostics in medical imaging, notably in scintigraphy.

the blocking of any metal ion of a paramagnetic metal such as iron, manganese, gadolinium, and their alloys, onto chelating particles, and the applications of these particles in diagnostics in medical imaging, notably such as contrasting agents in NMR imaging.

The use of an particle mentioned above for the preparation of a pharmaceutical composition, notably for the treatment of AIDS, being thus susceptible of presenting hydroxamic groups in the form of a sustained release.

According to a third aspect, the present invention also covers compositions, in particular cosmetic compositions, pharmaceutical compositions, agro-foodstuff compositions, liquid treatment compositions, in particular for the treatment of water, characterised in that they comprise small-sized particles comprising hydroxamic groups on the surface thereof, such as defined above or such as they result from the following description in relation to the Examples which make up an integral part of the present invention.

According to a fourth aspect, the present invention also relates to a method of preparation of these small-sized particles, characterised in that it comprises a first step according to which the interfacial cross-linking is carried out of a mixture of at least one protein and at least one polysaccharide, with a polyfunctional acylating cross-linking agent in order to obtain small-sized particles comprising, at least on the surface thereof, amide functions and ester functions and optionally also anhydride functions, and, in a second step, these cross-linked small-sized particles are allowed to react with hydroxylamine in an alkaline medium in order to cause rupture at least of ester bonds and optionally anhydride bonds with the linking of hydroxamic groups, which particles are recovered and which are thus capable of carrying out the chelation of metal ions.

According to a fifth aspect, the present invention also covers a method of trapping metal ions, characterised in that it comprises the use of small-sized particles according to the invention, bearing hydroxamic groups on the surface thereof, which are placed in contact with a medium containing at least one metal ion that is sought to remove from this medium by chelation with the hydroxamic groups and after a period of contact sufficient for carrying out the chelation, the thus-chelated small-sized particles are separated from this medium which are recovered.

In a further step, it is possible to recover the microspheres loaded with metal ions by carrying out a dechelation in the following manner: the chelating microspheres having chelated a metal ion are placed in suspension in a solution of demineralised water, for a duration of time between 15 minutes and 24 hours, preferably for a duration of time between 2 and 6 hours, at an acidic pH the exact value of which depends upon the ion to be dechelated, maintained throughout the whole of the treatment at a bound value, by using a strong acid (hydrochloric acid, nitric acid, etc . . . ).

According to a sixth aspect, the present invention also covers a method of controlled release of a metal ion in a given medium, comprising the prior preparation of small-sized particles according to the invention and which comprise hydroxamic groups engaged in chelates with the metal ion that is desired to release into the medium, and placing these small-sized particles thus loaded with this chelated metal ion to be released in contact with the medium in which this release must be effected, for a period of time of contact sufficient to carry out the release of the metal ion. In particular, it will be possible for this medium to be constituted by the skin of an animal, preferably the skin of a human being. As metal to be released, it will be preferred to use copper, selenium, zinc, silicon, germanium given the advantageous activities that these metals procure in the organism, and in particular on the skin.

According to a seventh aspect, the present invention also enables carrying out a cosmetic treatment or a therapeutic treatment of an animal, preferably a human being, according to which method small-sized particles according to the invention comprising hydroxamic groups on the surface thereof which are free or engaged in chelates with metal ions, are delivered to this human being or this animal on the area sought after, depending on whether the chelation of metal ion(s) present in the area of placing in contact of the animal is sought after, in order to remove these metal ions, or on the contrary, to release these metal ions in said zone of the animal.

Thus, the invention enables solving the whole of the technical problems set forth above in a simple manner, which is little costly, and which is usable on an industrial scale, in particular on a cosmetic, pharmaceutical or agro-foodstuff scale.

Furthermore, the invention comprises any characteristic which appears to be novel with respect to any state of the art, in its generality, and which results from the description taken in its entirety, including the Examples which make up an integral part of the invention in its most general means and functions as understandable to a person skilled in the art.

In the Examples, all the proportions are given by weight unless otherwise indicated, the temperature is ambient temperature or is given in degrees Celsius, and pressure is atmospheric pressure unless otherwise indicated.

EXAMPLE 1 OF THE INVENTION

General Preparation Of Chelating Microspheres From Atelocollagen a) An aqueous solution (2 kg) comprising 18 g/kg of atelocollagen and 48 g/kg of anhydrous sodium carbonate is prepared; x g/kg of a polysaccharide X is added to this solution under mechanical stirring which is kept up until a perfectly homogeneous solution is obtained.

b) The pH of this solution is adjusted to 9.8 by 6N hydrochloric acid and 6N sodium hydroxide;

c) 400 g of terephthalic acid dichloride are dispersed in 8 liters of a fatty acid ester (Dragoxat®, Dragoco, Germany).

d) In a vessel refrigerated at 6° C., 300 ml of sorbitan trioleate (Span 85, ICI, UK) are dispersed in 5.7 l of Dragoxat® e) The solution prepared in b) is poured into the vessel with mechanical stirring. The solution prepared in c) is then added to the whole with mechanical stirring and the whole is stirred for 10 minutes by a stirring system of the Ultra Turax® type which stirs at 7000 rpm. A reduced mechanical stirring (by about 20%) is kept up for a further 25 minutes.

f) The spheres are then separated from the fatty acid ester medium by natural or forced decanting. A moderate centrifugation (1000 rpm for 5 minutes) is sufficient to effect a correct separation.

g) Several washings were then carried out in order to remove any trace of fatty acid ester from around the microspheres thus prepared. The microspheres are separated from the washing medium by natural or forced decanting.

h) With moderate mechanical stirring, the recovered microspheres (about 2 kg) are then suspended in a solution of 2 liters of ethanol in which 80 g of hydroxylamine hydrochloride have been dissolved beforehand. A solution of 1 liter of ethanol in which 80 g of sodium hydroxide pellets were dissolved beforehand is then added to the whole.

i) The whole is kept stirred for 15 minutes, the microspheres are then separated from the medium, and then washed with two successive baths of ethanol, followed by two washings with demineralised water. The microspheres are separated from the washing medium by natural or forced decanting.

j) a yield can then be calculated based upon the amount of aqueous phase used (here, 2 Kg).

k) The recovered microspheres are then optionally placed in contact with the aqueous solution of a salt of the cation (silver salts for example) the complexation of which is desired for 1 hour at 6° C., and then are washed by two washings with demineralised water.

l) The recovered microspheres (cation charged, step k, or non-charged, step j) are then optionally placed in suspension in a gel (hydrophilic, lipophilic, or of silicone type), optionally containing preservatives, which can be used in any cosmetic, pharmaceutical or agro-foodstuff preparation. These microspheres can also be dried (by lyophilisation or atomisation for example) and then sterilised by radiation, in order to be used in all types of applications in which dried forms would be preferred (use in oily solutions or silicones for example).

In this example, by not adding any polysaccharide (x=0), the industrial yield obtained in j) is 0%, i.e. that it was not possible to recover the microspheres after the hydroxylamine/sodium hydroxide treatment. In this case, the process was carried out in its entirety at 20° C.; this temperature can be modified from 4° C. to 40° C. but no improvement was obtained as regards the industrial yield at these different temperatures.

When different polysaccharides are used, every other parameter being identical, microspheres of size between 1 and 100 $\mu$m are observed under optical microscopy, and the yields obtained as described in j) become significant:

|  | Polysaccharides used (X) | Quantities used (x) | Yields(%) j) |
|---|---|---|---|
| I1 | None | 0 | 0 |
| I2 | Chitosan | 3 | 92 |
| I3 | Chitosan | 8 | 78 |
| I4 | Chondroitine Sulphate | 6 | 58 |
| I5 | Chondroitine Sulphate | 7.5 | 53 |
| I6 | Chondroitine Sulphate | 47.5 | 52 |
| I7 | Hyaluronic acid | 7.5 | 20 |
| I8 | Hydroxyethyl cellulose | 7.5 | 46 |
| I9 | Carraghenan | 7.5 | 42 |
| I10 | Alginate | 7.5 | 7 |
| I11 | Pectin | 7.5 | 27 |

EXAMPLE 2 OF THE INVENTION

Variants Of Preparation Of The Chelating Microspheres

1) The aqueous solution prepared in Example Ia can contain from 5 to 25 g/kg of atelocollagen, it being possible for this collagen to be of mammalian origin or of fish origin, from 10 to 100 g/kg of anhydrous sodium carbonate and from 1 to 100 g/kg of polysaccharide.

2) It is possible to use a buffer other than the carbonate buffer (phosphate, borate, ammonia, succinate, etc. . . . ), it being possible for the pH adjusted in Ib to be between 7.5 and 12 for the proteins other than plant proteins, and between 4.5 and 8, for plant proteins.

3) It is possible to lead the whole of the operation at temperatures between 4° C. and 40° C., and preferably at temperatures between 6 and 25° C.

4) The polysaccharide used- is preferably selected from the polysaccharides described in Example I, and is more preferably chitosan, but various other polysaccharides can be used in the invention: chitosan and its derivatives, glycosaminoglycans (chondroitine sulphate, hyaluronic acid, dermatan sulphate, heparan sulphate, high and low molecular weight heparins, keratan sulphate), cellulose and its derivatives, starch and its derivatives, carrageenins, alginates, pectins, xanthan, guar, carobe, karaya gums, gum Arabic, scleroglucans, gluco- and galacto-manans, arabinogalactans, pentosans and dextrans and derivatives thereof.

5) The proteins which can be used are collagen, including marine collagen, atelocollagen including marine atelocollagen, moderate hydrolysates of collagen, including marine collagen hydrolysates, gelatine, including marine gelatine, in a basic buffer (pH adjusted in Ib to values between 7.5 and 12), or plant proteins in a buffer close to neutrality even slightly acidic (pH adjusted in Ib to values between 4.5 and 8). Plant proteins can be varied and are for example extracted from leguminous or proteagenous plants, in particular the following plants: lupin (genus Lupinus), soya (genus Glycine), pea (genus Pisum), chick pea (genus Cicer), lucerne (genus Medicago), bean (genus Vicea), lentil (genus Lens), bean (genus Phaseolus), sesame (genus Sesamum), rape (genus Brassica), or sunflower (genus Elientus), or even cereals such as, for example, wheat, maize, barley, malt, oats.

These plant proteins can be used in the form of a powdery preparation such as flours, concentrates, isolates, or liquid preparations such as soya milks. By using a protein isolate from soya, the yield of production obtained as described in Ij) is 20%.

In every case, a polysaccharide, preferably chitosan or one of its derivatives, is added to the solution Ia during the preparation of the microspheres.

6) The size of the microspheres obtained at the end of the process is adjusted by modifying the speed of stirring in Ie. The size is 900 μm for a rotation speed of 400 rpm and 1 μm or less for rotation speeds of 15,000–20,000 rpm.
7) The amount of hydroxylamine and sodium hydroxide described in Ih can vary within quite significant proportions; the amount is preferably between 10 g/kg and 400 g/kg, more preferably between 30 g/kg and 240 g/kg
8) The hydroxylamine hydrochloride can also be dissolved in 2 liters of water instead of 2 liters of ethanol as described in Example 1. Similarly, sodium hydroxide can be dissolved in water instead of ethanol and the amount of sodium hydroxide can be different. This amount must be necessary and sufficient in order to obtain a final reaction pH of the small-sized particles (such as microspheres or nanospheres, or microcapsules or nanocapsules) in the particles/sodium hydroxide/hydroxylamine mixture of between 9 and 13.5, more preferably between 9.5 and 13.
9) The cross-linked particles comprising hydroxamic groups on the surface are separated by any means such as decantation or centrifugation which are recovered. These particles have a very good chelating capacity and a good mechanical and biological resistance, notably as regards enzymatic lysis.

EXAMPLE 3 OF THE INVENTION

Currently Preferred Method Of Preparation Of Small-Sized Chelating Particles

First step a) 2 kg of an aqueous solution comprising 18 g/kg of atelocollagen of marine origin is prepared, for example obtained from non-pigmented fish skins such as described in the preceding document by the Applicant U.S. Pat. No. 5,420,248, and 48 g/kg of anhydrous sodium carbonate.

A solution of chitosan prepared beforehand is added into this solution so as to obtain a final concentration of 3 g/kg of chitosan in this aqueous solution.

This addition is carried out with mechanical stirring which is kept up until a perfectly homogeneous solution is obtained.

b) The pH of this solution is adjusted to 9 with 6N hydrochloric acid and 6N sodium hydroxide;

c) 400 g of terephthalic acid dichloride are dispersed in 8 liters of a fatty acid ester, for example Dragoxat® (Dragoco, Germany);

d) In a vessel refrigerated at 6° C., 300 ml of sorbitan trioleate, for example Span 85® (ICI, United Kingdom), are dispersed in 5.7 l of Dragoxat®;

e) The solution prepared in b) is poured into the vessel with mechanical stirring. The solution prepared in e) is then added to the whole with mechanical stirring and the whole is stirred for 10 minutes by a stirring system of the Ultra Turax type stirring at 7000 rpm. A reduced mechanical stirring (by about 20%) is kept up for a further 25 minutes.

f) The spheres are then separated from the fatty acids medium by moderate centrifugation (100 rpm for 5 minutes). The size of the microspheres (which can be between 1 and 100 μm) in this case is about 50 μm.

g) Several washings are then carried out so as to remove any trace of fatty acid ester from around the microspheres thus prepared. These washings are carried out with the aid of mixtures of ethanol/surfactant such as Tween 20 from ICI, United Kingdom, mixtures of water/ethanol, and then demineralised water. The microspheres are separated from the washing medium by moderate centrifugation.

Second step h) With moderate mechanical stirring, the recovered microspheres, i.e. about 2 kg, are then placed in suspension in a solution of 2 liters of ethanol in which 80 g of hydroxylamine hydrochloride were dissolved beforehand.

A solution of 1 liter of ethanol in which 80 g of sodium hydroxide pellets were dissolved beforehand, is then added to the whole.

i) The whole is kept with stirring for 15 minutes, and then the microspheres are separated from the medium, and then washed with two successive baths of ethanol, followed by two washings with demineralised water.

The microspheres having hydroxamic groups on the surface thereof are separated from the washing medium by moderate centrifugation.

j) The yield, calculated from the amount of aqueous phase used, here 2 kg, is 92%.

k) The microspheres bearing hydroxamic groups on the surface can then advantageously be placed in suspension in a hydrophilic gel containing preservatives which can be stored for prolonged periods of time whilst waiting for the use for example in cosmetics, pharmaceuticals or agrofoodstuff preparations.

EXAMPLE 4 OF THE INVENTION

Variants Of Preparation Of The Chelating Microspheres

The chelating microspheres can equally encapsulate hydrosoluble substances (e.g.: flavonoids, vitamin C, plant extracts, etc . . . ), insoluble substances (e.g.: insoluble particles, pigments, etc . . . ), or liposoluble substances (vitamin A or E and derivatives thereof, essential oils, etc . . . ). In this case, these solutions are added to the solution described in Ia with very strong mechanical stirring (Ultra-Turax type, 10,000 rpm for 5 minutes), so as to ensure a good dispersion of the whole.

EXAMPLE 5 OF THE INVENTION

Chelation Kinetics

The chelating microspheres prepared according to I5 are lyophilised and used to evaluate the kinetics to chelate metal ions; iron (III) is taken as model cation.

100 mg of these chelating microspheres are added to 20 ml of a solution prepared beforehand, containing 300 mg/l of [$FeCl_3.6H_2O$] the pH of which was adjusted to 2.3 with nitric acid.

After different periods of contact, with mechanical stirring, solutions are taken, filtered in order to remove the chelating microspheres loaded with iron, and the content of the filtrate is analysed by atomic absorption spectrometry (Spectro AA620 Plus, Perkin Elmer) at a wavelength of 248.3 nm, by carrying out an average over 4 successive measurements.

The results are expressed as a percentage with respect to the amount of iron III placed in contact with the chelating microspheres. The results are the following:

| Time | % chelation |
|---|---|
| 2 min | 58.2 |
| 5 min | 68 |
| 10 min | 74.4 |
| 20 min | 76.3 |
| 40 min | 77.3 |
| 60 min | 77.3 |
| 5 hours | 76.8 |

EXAMPLE 6 OF THE INVENTION

Influence Of The pH Upon The Chelation

The chelating microspheres prepared according to I5 are lyophilised and used to evaluate the influence of the pH upon the chelation of metal ions; calcium is taken as model cation. 100 mg of these chelating microspheres are added to 20 ml of a solution prepared beforehand from calcium chloride, containing increasing amounts of $Ca^{2+}$ expressed in (mg/l), the pH of which was adjusted to different values by the addition of hydrochloric acid.

After 3 hours of contact, with mechanical stirring, solutions are taken, filtered to remove the chelating microspheres loaded with calcium, and the content of the filtrate is analysed by atomic absorption spectrometry (Spectro AA620 Plus, Perkin Elmer) at a wavelength of 422.7 nm, by carrying out an average over 4 successive measurements.

The results are expressed as a percentage with respect to the amount of calcium placed in contact with the chelating microspheres. The yields of chelation are the following:

| | Initial concentrations of $Ca^{2+}$ | |
|---|---|---|
| pH | 27 ppm | 136 ppm |
| 2.3 | 1.3 | 0 |
| 3 | 61.2 | 23.9 |
| 4 | 71.5 | 33.7 |
| 5.1 | 73.2 | 32.3 |

EXAMPLE 7 OF THE INVENTION

Reversibility Of The Chelation

The chelating microspheres prepared according to I5 are lyophilised and used to evaluate the reversibility of the chelation of metal ions; calcium is taken as model cation.

107 mg of these chelating microspheres are added to 20 ml of a solution prepared beforehand from calcium chloride, containing 82.4 ppm (mg/l) of $Ca^{2+}$, the pH of which is adjusted to 5.0 with nitric acid.

After 2 hours of contact, with mechanical stirring, the solution is filtered so as to evaluate the amount of $Ca^{2+}$ chelated by the products of the invention. The yield of chelation is expressed as a function of the amount of $Ca^{2+}$ placed in contact with the chelating microspheres. The yield of chelation is 50%.

After filtration, these chelating microspheres are placed in contact with an aqueous solution the pH of which was adjusted beforehand to 2.3 with nitric acid. After 2 hours of contact, with mechanical stirring, the solution is filtered so as to evaluate the amount of $Ca^{2+}$ liberated.

The yield of regeneration is expressed as a percentage with respect to the amount of calcium chelated beforehand. The yield of regeneration is 79%.

These chelating microspheres are then placed again in an aqueous solution of calcium chloride the pH of which is adjusted to 5.0 with nitric acid, containing 82.4 ppm of calcium.

After 2 hours of contact, with mechanical stirring, the solution is filtered so as to remove the chelating microspheres loaded with calcium, and the content of the filtrate is analysed.

The results are expressed as a percentage with respect to the amount of calcium placed in contact with the chelating microspheres. The yield of chelation is 34.6%.

It is therefore possible to regenerate the products of the invention the use of which can consequently be envisaged in various industrial applications.

EXAMPLE 8 OF THE INVENTION

Iron(III) Chelation

The chelating microspheres prepared according to I5 are lyophilised and used to evaluate their capacity to chelate iron(III).

100 mg of these chelating microspheres are added to 20 ml of a solution prepared beforehand from $[FeCl_3.6H_2O]$, containing determined amounts of $Fe^{3+}$ (expressed in mg/l i.e. in ppm) the pH of which was adjusted to 2.3 with nitric acid.

After 3 hours of contact, with mechanical stirring, solutions are taken, filtered so as to remove the chelating microspheres loaded with iron, and the content of the filtrate is analysed by Atomic absorption spectrometry (Spectro AA620 Plus, Perkin Elmer) at a wavelength of 248.3 nm, by carrying out an average over 4 successive measurements.

The results are expressed as a percentage with respect to the amount of $Fe^{3+}$ placed in contact with the chelating microspheres. The results are the following:

| Concentration of $Fe^{3+}$ in the solution used (ppm/l) | chelation |
|---|---|
| 2.95 | 92.2 |
| 4.41 | 88.4 |
| 9.01 | 87.2 |
| 13.8 | 81.8 |
| 19.2 | 80.6 |
| 38.2 | 73.2 |
| 56.8 | 70.7 |
| 73.2 | 67.1 |
| 103.2 | 75.3 |
| 111.5 | 58.8 |

EXAMPLE 9 OF THE INVENTION

Chelation Of Iron(II)

The chelating microspheres prepared according to I2 are lyophilised and used to evaluate their capacity to chelate iron(II).

100 mg of these chelating microspheres are added to 20 ml of a solution prepared beforehand from $FeCl_2$, containing determined amounts of $Fe^{2+}$ (expressed in mg/l i.e. in ppm) the pH of which was adjusted to 3.7 with hydrochloric acid.

After 3 hours of contact, with mechanical stirring, solutions are taken, filtered so as to remove the chelating microspheres loaded with iron, and the content of the filtrate is analysed by Atomic absorption spectrometry (Spectro AA620 Plus, Perkin Elmer) at a wavelength of 248.3 nm, by carrying out an average over 4 successive measurements.

The results are expressed as a percentage of chelation with respect to the amount of $Fe^{2+}$ placed in contact with the chelating microspheres. The results are the following:

| Concentration of $Fe^{2+}$ (ppm) | chelation |
|---|---|
| 51 | 89.5 |
| 127 | 44.2 |
| 248 | 23.9 |
| 511 | 8 |

EXAMPLE 10 OF THE INVENTION

Silver Chelation And Use Of The Product Of The Invention As Anti-Bacterial And Anti-Fungal Agent The chelating microspheres prepared according to I2 are lyophilised and used to evaluate their capacity to chelate silver.

100 mg of these chelating microspheres are added to 20 ml of a solution prepared beforehand from $AgNO_3$, containing determined amounts of $Ag^+$ (expressed in mg/l i.e. in ppm) the pH of which was adjusted to 4.7 with nitric acid.

After 3 hours of contact, with mechanical stirring, solutions are taken, filtered so as to remove the chelating microspheres loaded with silver, and the content of the filtrate is analysed by Atomic absorption spectrometry (Spectro AA620 Plus, Perkin Elmer) at a wavelength of 328.1 nm, by carrying out an average over 4 successive measurements.

The results are expressed as a percentage of chelation with respect to the amount of $Ag^+$ placed in contact with the chelating microspheres. The results are the following:

| Concentration of $Ag^+$ (ppm) | chelation |
|---|---|
| 56 | 79.5 |
| 115 | 78.5 |
| 280 | 55.2 |
| 552 | 30.2 |

After silver chelation, the products of the invention are purified by dialysis (so as to remove the non-complexed silver ions), lyophilised and analysed: 100 mg of chelating microspheres contain 3.84 mg of $Ag^+$. These chelating microspheres are then used at 160 mg per liter as preservative in a classical bacterial and fungal over-contamination test, and this enables evaluating the bactericidal and fungicidal power of any product on 2 bacterial strains and 2 fungal strains for 28 days, after initial sowings at the rate of 1 to 2 million of germs per gram.

| Nature of the micro-organism | Concentration of micro-organisms (germs/g) | | |
|---|---|---|---|
| | T0 | T7 days | T28 days |
| Pseudomonas aeruginosa | $1.7 \cdot 10^6$ | 9 | <1 |
| Staphylococcus aureus | $1.0 \cdot 10^6$ | <1 | <1 |
| Candida albicans | $1.2 \cdot 10^6$ | <1 | <1 |
| Aspergillus niger | $9 \cdot 10^5$ | $4 \cdot 10^3$ | <10 |

The product of the invention loaded with silver is therefore microbiocidal, and can therefore be used in numerous cosmetic, pharmaceutical even food applications. The product of the invention can also be used for treating solutions which are sensitive to any sterilising treatment, by placing the solutions to be treated in contact with microspheres loaded with silver, followed by a filtration of the treated solution so as to remove the particles and to recover the disinfected solution.

EXAMPLE 11 OF THE INVENTION

Chelation Of Copper (II)

The chelating microspheres prepared according to I2 are lyophilised and used to evaluate their capacity to chelate copper(II).

100 mg of these chelating microspheres are added to 20 ml of a solution prepared beforehand from $CuCl_2$, containing determined amounts of $Cu^{2+}$ (expressed in mg/l i.e. in ppm) the pH of which was adjusted to 4.6 with hydrochloric acid.

After 3 hours of contact, with mechanical stirring, solutions are taken, filtered so as to remove the chelating microspheres loaded with copper, and the content of the filtrate is analysed by Atomic absorption spectrometry (Spectro AA620 Plus, Perkin Elmer) at a wavelength of 324.8 nm, by carrying out an average over 4 successive measurements.

The results are expressed as a percentage of chelation with respect to the amount of $Cu^{2+}$ placed in contact with the chelating microspheres. The results are the following:

| Concentration of $Cu^{2+}$ (ppm) | chelation |
|---|---|
| 41 | 95.2 |
| 106 | 70.5 |
| 218 | 35.6 |
| 426 | 17.9 |

EXAMPLE 12 OF THE INVENTION

Chelation Of Calcium

The chelating microspheres prepared according to I2 are lyophilised and used to evaluate their capacity to chelate calcium.

100 mg of these chelating microspheres are added to 20 ml of a solution prepared beforehand from $CaCl_2$, containing determined amounts of $Ca^{2+}$ (expressed in mg/l i.e. in ppm) the pH of which was adjusted to 5.1 by hydrochloric acid.

After 3 hours of contact, with mechanical stirring, solutions are taken, filtered so as to remove the chelating microspheres loaded with calcium, and the content of the filtrate is analysed by Atomic absorption spectrometry (Spectro AA620 Plus, Perkin Elmer) at a wavelength of 422.7 nm, by carrying out an average over 4 successive measurements.

The results are expressed as a percentage of chelation with respect to the amount of $Ca^{2+}$ placed in contact with the chelating microspheres. The results are the following:

| Concentration of $Ca^{2+}$ (ppm) | chelation |
|---|---|
| 12 | 72.9 |
| 25 | 67 |
| 66 | 52.6 |
| 130 | 31.6 |
| 273 | 18.2 |

EXAMPLE 13 OF THE INVENTION

Chelation Of Zinc

The chelating microspheres prepared according to I2 are lyophilised and used to evaluate their capacity to chelate zinc.

100 mg of these chelating microspheres are added to 20 ml of a solution prepared beforehand from $ZnCl_2$, containing determined amounts of $Zn^{2+}$ (expressed in mg/l i.e. in ppm) the pH of which was adjusted to 5 with hydrochloric acid.

After 3 hours of contact, with mechanical stirring, solutions are taken, filtered so as to remove the chelating microspheres loaded with zinc, and the content of the filtrate is analysed by Atomic absorption spectrometry (Spectro AA620 Plus, Perkin Elmer) at a wavelength of 213.9 nm, by carrying out an average over 4 successive measurements.

The results are expressed as a percentage of chelation with respect to the amount of $Zn^{2+}$ placed in contact with the chelating microspheres. The results are the following:

| Concentration of $Zn^{2+}$ (ppm) | chelation |
|---|---|
| 19 | 93.5 |
| 59 | 74.5 |
| 164 | 42.7 |
| 322 | 24.0 |

EXAMPLE 14 OF THE INVENTION

Chelation Of Aluminium

The chelating microspheres prepared according to I2 are lyophilised and used to evaluate their capacity to chelate de aluminium.

100 mg of these chelating microspheres are added to 20 ml of a solution prepared beforehand from $AlCl_3$, containing determined amounts of $Al^{3+}$ (expressed in mg/l i.e. in ppm) the pH of which was adjusted to 4.1 with hydrochloric acid.

After 3 hours of contact, with mechanical stirring, solutions are taken, filtered so as to remove the chelating microspheres loaded with aluminium, and the content of the filtrate is analysed by Atomic absorption spectrometry (Spectro AA620 Plus, Perkin Elmer) at a wavelength of 309.3 nm by carrying out an average over 4 successive measurements.

The results are expressed as a percentage of chelation with respect to the amount of $Al^{3+}$ placed in contact with the chelating microspheres. The results are the following:

| Concentration of $Al^{3+}$ (ppm) | chelation |
|---|---|
| 20 | 93 |
| 181 | 21.5 |

EXAMPLE 15 OF THE INVENTION

Chelation Of Other Metal Ions

The chelating microspheres prepared according to I2 were tested as described in the Examples above on a large number of metal ions, and are capable of efficiently trapping a large number of said ions: the sodium, potassium, magnesium, manganese, chromium, nickel, cadmium, lead, gold, silicon, germanium ions have therefore for example been tested with success, which signifies that this list is non-limiting and that the trapping capacity of the chelating microspheres, products of the invention, is not limited to the metal ions evaluated but to any metal ion which carries one or more positive charges.

EXAMPLE 16 OF THE INVENTION

Applications In Oily Media

The chelating microspheres prepared according to I2 are lyophilised and used to evaluate their capacity of chelation in an essential oil which is desired to detoxify and which contains significant amounts of copper.

100 mg of these chelating microspheres are added to 10 ml of a solution prepared beforehand, containing an amount of copper which was evaluated beforehand by Atomic absorption spectrometry at 1.44 mg/l (i.e. 1.44 ppm).

After 3 hours of contact, with mechanical stirring, solutions are taken, filtered so as to remove the chelating microspheres loaded with copper, and the content of the filtrate is analysed by Atomic absorption spectrometry (Spectro AA620 Plus, Perkin Elmer) at a wavelength of 324.8 nm, by carrying out an average over 4 successive measurements.

The amount of residual copper after chelation is 0.04 ppm and the percentage of chelation with respect to the amount of copper placed in contact with the chelating microspheres is therefore 97%.

It is therefore possible to remove the metal ions from oily preparations such as essential oils, from solvents, from silicones, or from complex organic media, and for example to <<decontaminate>> by this technique such media loaded with copper, iron, aluminium, lead, nickel, compounds the content of which must be very rigorously controlled, before putting on the market substances which may contain them. These metal ions may originate from preparation methods (the use of catalysts for example), or may be present as non-desired contaminants (pollutants for example).

EXAMPLE 17 OF THE INVENTION

Applications To Anti-Protease Effects

The chelating microspheres prepared according to I2 are used to evaluate their capacity to inhibit enzymatic activities of the protease type for cosmetic, pharmaceutical or agrofoodstuff applications. Proteases are in fact involved in a large number of problems in human health (metastasis cancers, AIDS . . . ) and dermatological problems (photo-induced ageing of the skin tissues by an exaggerated synthesis of protease activity when exposed to weak doses of UV).

In order to study the capacity of the products of the invention to inhibit these protease activities, a bacterial collagenase (Clostridium histolyticum) is used as protease activity model; this enzyme is used in solution in a Tris-$CaCl_2$ buffer pH 7.4 at the rate of 15 U/ml of buffer, and then placed in contact with native bovine collagen (2 mg/ml of buffer). The protease activity is evaluated by evaluating at regular intervals the hydrolysed collagen fragment which diffuse with a continuous flow though a dialysis membrane. The amount of collagen hydrolysed is calculated from the determination of hydroxyproline, a characteristic amino acid of collagen.

The chelating microspheres of the invention are placed at the rate of 0.28 mg/ml of the buffer solution containing the native collagen and the collagenase as described above, and are evaluated for their capacity to inhibit this protease.

The results, expressed in % of degradation of collagen, are the following:

| Time (hours) | Degradation of collagen (%) Control | Degradation of collagen (%) With product of the invention | Calculation of the amount of inhibition of the protease With product of the invention |
|---|---|---|---|
| 0 | 0 | 0 | 0 |
| 2 | 9.4 | 6.2 | 34 |
| 4 | 33.7 | 19.8 | 41 |
| 6 | 50 | 33.5 | 33 |
| 8 | 64.2 | 46.6 | 27 |

It is therefore possible to chelate calcium ions, enzymatic cofactors which are essential for the proteases, by using the products of the invention, to inhibit these proteases, and to thus envisage the use of the products of the invention for cosmetic, pharmaceutical and agro-foodstuff applications.

EXAMPLE 18 OF THE INVENTION

Applications To Anti-Tyrosinase Effects

Ceruleoplasmin, ferroxidase, cytochrome C oxidase, superoxide dismutase, ascorbate oxidase, tyrosinase, dopa beta hydroxylase, mono amine oxidase, . . . are enzymes which possess an essential enzymatic cofactor: copper. Chelating it enables inhibiting certain enzymatic activities.

Tyrosinase is therefore used as a model in this evaluation, which consists in studying the capacity of the products of the invention to chelate copper and to inhibit these enzymatic activities.

The chelating microspheres prepared according to I2 or I5 are used to evaluate their capacity to inhibit tyrosinase, for cosmetic applications (depigmentation, pigmentation), pharmaceutical applications or agro-foodstuff applications (browning of food). For this, an aqueous solution of mushroom tyrosinase (1460 U/ml) is placed in contact with a solution of L-DOPA in PBS buffer (Phosphate Buffered Saline), in the presence or not of increasing amounts of the products of the invention (I2 and I5), the formation of dopachromium, product of the reaction of L-Dopa by tyrosinase being followed by spectrophotometry at 475 nm.

The chelating microspheres are evaluated for their capacity to inhibit tyrosinase. The results are the following:

| | Tyrosinase inhibition (%) |
|---|---|
| Amount of product of the invention I2 (mg/ml) | |
| 0 | 0 |
| 0.5 | 48.8 |
| 0.7 | 58.8 |
| 1.0 | 62.2 |
| 1.5 | 65.0 |
| 2.0 | 66.6 |
| Amount of product of the invention I5 (mg/ml) | |
| 0 | 0 |
| 0.5 | 63.8 |
| 1.0 | 78.8 |
| 2.0 | 87.7 |

It is therefore possible to chelate copper ions which are essential enzymatic cofactors of certain enzymes including the tyrosinases, by using the products of the invention to inhibit these enzymes, and to thus envisage the use of the products of the invention for cosmetic, pharmaceutical and agro-foodstuff applications.

EXAMPLE 19 OF THE INVENTION

Applications To Inhibit The Radical Degradation Of Hyaluronic Acid, Glycosaminoglycan Implied In The Moisturisation Of The Human Dermis The chelating microspheres prepared according to I2 are used to evaluate their capacity, via the trapping of ferrous iron Fe2+, to inhibit the radical degradation of hyaluronic acid, glycosarinoglycan implied in the moisturisation of the human dermis, which is therefore a particularly important target to protect in cosmetic and dermo-pharmaceutical applications.

This protection against the photo-ageing can be demonstrated in the following way:

A 10 g/l solution of hyaluronic acid of high molecular weight (>1,000,000 g/mol or Daltons) is prepared in demineralised water. To this solution is added an amount of Fe2+ of 620 ppm. A drop in the viscosity is noted with time, which represents the radical degradation of hyaluronic acid and its depolymerisation into elements of lower molecular weight. This depolymerisation which induces a drop in viscosity is accelerated in the presence of a classical chelating agent such as EDTA, which chelates iron but gives it unexpected pro-radical properties.

Other chelating agents which are conventionally used in cosmetics were used and compared to the chelating microspheres, for their capacity to reduce the radical degradation of hyaluronic acid. Indices of protection, expressed in % of protection, are calculated by carrying out a ratio of the drop in viscosity observed by the presence of iron Fe2+ (620 ppm) in the presence of the chelating agent studied, and the drop in viscosity observed with and without iron Fe2+.

The results obtained are the following:

| Chelating agent | Concentration used | Index of protection (%) |
|---|---|---|
| Transferrin | 125 mg/l | 8.7 |
| Lactoferrin | 133 mg/l | 25 |
| Ferritin | 319 mg/l | 0 |
| Hydroxylamine | 6.25 g/l | 0 |
| 2-furyldioxime | 1.56 g/l | 23.5 |
| 2-furyldioxime | 9.37 g/l | 50 |
| Chelating microspheres | 0.31 g/l | 33.3 |
| Chelating microspheres | 0.94 g/l | 70 |
| Chelating microspheres | 1.56 g/l | 83.3 |

It results from these results that the products of the invention are capable of blocking iron $Fe^{2+}$ in a very efficient manner, through inhibiting the oxidising properties of this metal. The protection of biological molecules present within the cutaneous structures during an oxidative stress generated by the presence of metals and/or UV rays therefore enables using the products of the invention in cosmetological and dermo-pharmaceutical applications which seek to prevent and fight against the ageing of the skin tissues induced by repeated oxidative stresses such as photo-induced ageing, free radicals, pollution, etc . . . , and against loosening of the tissues observed in vivo.

In these examples of formulation, the names of the compounds are given according to the international nomenclature imposed in cosmetics, described in the INCI dictionary.

EXAMPLE 20

Use Of The Products Of The Invention In Cosmetic Or Pharmaceutical Formulations Of The Oil-In-Water Type

| | Formulation 20a | |
|---|---|---|
| A | Water | qsp 100 |
| | Butylene Glycol | 2 |
| | Glycerine | 3 |
| | Sodium Dihydroxycetyl Phosphate, Isopropyl Hydroxycetyl Ether | 2 |
| B | Glycol Stearate SE | |
| | Triisononaoin | 5 |
| | Octyl cocoate | 6 |
| C | Butylene Glycol Methylparaben, Ethylparaben, Propylparaben, pH adjusted to 5.5 | 2 |
| D | Products of the invention | 0.01–10% |

| | Formulation 20b | |
|---|---|---|
| A | Water | qsp 100 |
| | Butylene Glycol | 2 |
| | Glycerine | 3 |
| | Polyacrylamide, Isoparaffin Laureth-7 | 2.8 |
| B | Butylene Glycol, Methylparaben, Ethylparaben, Propylparaben | 2 |
| | Phenoxyethanol, Methylparaben, Propylparaben, Butylparaben, Ethylparaben | 2 |
| | Butylene Glycol | 0.5 |
| C | Products of the invention | 0.01–10% |

| | Formulation 20c | |
|---|---|---|
| A | Carbomer | 0.50 |
| | Propylene Glycol | 3 |
| | Glycerol | 5 |
| | Water | qsp 100 |
| B | Octyl Cocoate | 5 |
| | Bisabolot | 0.30 |
| | Dimethicone | 0.30 |
| C | Sodium Hydroxide | 1.60 |
| D | Phenoxyethanol, Methylparaben, Propylparaben, Butylparaben, Ethylparaben | 0.50 |
| E | Perfume | 0.3 |
| F | Products of the invention | 0.01–10% |

EXAMPLE 21 OF THE INVENTION

Use Of The Products Of The Invention In A Formulation Of The Water-In-Oil Type

| | | |
|---|---|---|
| A | PEG 30 - dipolyhydroxystearate | 3 |
| | Capric Triglycerides | 3 |
| | Cetearyl Octanoate | 4 |
| | Dibutyl Adipate | 3 |
| | Grape Seed Oil | 1.5 |
| | Jojoba Oil | 1.5 |
| | Phenoxyethanol, Methylparaben, Propylparaben, Butylparaben, Ethylparaben | 0.5 |
| B | Glycerine | 3 |
| | Butylene Glycol | 3 |
| | Magnesium Sulphate | 0.5 |
| | EDTA | 0.05 |
| | Water | qsp 100 |
| C | Cyclomethicone | 1 |
| | Dimethicone | 1 |
| D | Perfume | 0.3 |
| E | Product of the invention | 001–10% |

EXAMPLE 22 OF THE INVENTION

Use Of The Products Of The Invention In A Shampoo Or Shower Gel Type Formulation

| | | |
|---|---|---|
| A | xanthan Gum | 0.8 |
| | Water | qsp 100 |
| B | Butylene Glycol, Methylparaben, Ethylparaben, Propylparaben | 0.5 |
| | Phenoxyethanol, Methylparaben, Propylparaben, Butylparaben, Ethylparaben | 0.5 |
| C | Citric acid | 0.8 |
| D | Sodium Laureth Sulphate | 40.0 |
| E | Product of the invention | 0.01–10% |

EXAMPLE 23 OF THE INVENTION

Use Of The Products Of The Invention In A Lipstick Type Formulation And Other Anhydrous Products

| | | |
|---|---|---|
| A | Mineral Wax | 17.0 |
| | Isostearyl Isostearate | 31.5 |

-continued

| | | |
|---|---|---|
| | Propylene Glycol Dipelargonate | 2.6 |
| | Propylene Glycol Isostearate | 1.7 |
| | PEG 8 Beeswax | 3.0 |
| | Hydrogenated Palm Kernel Oil Glycerides, hydrogenated Palm Glyceride | 3.4 |
| | Lanolin Oil | 3.4 |
| | Sesame Oil | 1.7 |
| | Tribehenin | 1.7 |
| | Cetyl Lactate | 1.7 |
| | Mineral Oil, Lanolin Alcohol | 3.0 |
| B | Castor Oil | qsp 100 |
| | Titanium Dioxide | 3.9 |
| | CI 15850:1 | 0.616 |
| | CI 45410:1 | 0.256 |
| | CI 19140:1 | 0.048 |
| | CI 77491 | 2.048 |
| C | Product of the invention | 0.01–5 |

EXAMPLE 23 OF THE INVENTION

Use Of The Products Of The Invention In An Aqueous Gels Formulation (Eye Contours, Slimming Products, Etc . . . )

| | | |
|---|---|---|
| A | Water | qsp 100 |
| | Carbomer | 0.5 |
| | Butylene Glycol | 15 |
| | Phenoxyethanol, Methylparaben, Propylparaben, Butylparaben, Ethylparaben | 0.5 |
| B | Product of the invention | 0.01–10 |

EXAMPLE 25

Toxicology Studies Carried Out On The Products Of The Invention a) Oral toxicity The tests were carried out in following the protocol in accordance with the guidelines of the OECD in relation to the study of acute oral toxicity (No 401 of the Feb. 24, 1987) at maximal doses of 5 g/kg of body weight and did not cause any macroscopic lesion able to be attributed to a toxic effect of the product.

The products of the invention (Examples I2 and I5) used orally at lower doses at 5 g/kg therefore has zero toxicity.

b) Ocular irritation

The tests were carried out according to the official method by the decision of the May 3, 1990 (Journal Officiel de la République Frangaise of the Nov. 14, 1990) with the products of the invention (Examples I2 and I5) and did not cause any lesion of the iris or the cornea.

The products of the invention (Examples I2 and I5) instilled pure appeared to be non-irritant and the ocular tolerance can be considered to be as very good.

c) Cutaneous irritation

The tests were carried out according to the official method of the decision of the Feb. 1, 1982 (Journal Officiel de la République Francaise of the Feb. 21, 1982) with the products of the invention (Examples I2 and I5) and did not cause any irritating phenomena.

The products of the invention (Examples I2 and I5) instilled pure have appeared to be non-irritant and the cutaneous tolerance can be considered as excellent.

d) Research into the sensitising power

Maximisation tests were carried out according to a protocol adapted from the method described by MAGNUSSON and KLIGMAN (J. INVEST. DERM 1969, 52, 268–276).

The products of the invention (Examples I2 and I5) instilled pure did not cause any significant macroscopic reaction of a sensitisation reaction. They can be considered as hypoallergenic (Class I).

What is claimed is:

1. A particle selected from a micro particle and/or a nanoparticle having a surface which comprises, at least on the surface thereof, a wall composed of a mixture of at least one protein and at least one polysaccharide which are cross-linked, by interfacial cross-linking with a polyfunctional acylating cross-linking agent which forms at least amide and ester bonds, and optionally anhydride bonds, with amine, or hydroxyl or carboxyl functions of the protein and of the polysaccharide, said protein and said polysaccharide being present in said at least cross-linked wall in relative weight proportions sufficient to provide to said cross-linked wall resistance to degradation by hydroxylamine in an alkaline medium, and which comprises hydroxamic groups on the surface thereof for chelating metal ions.

2. The particle of claim 1, wherein the hydroxamic groups are bound on the surface by reaction of the particles, cross-linked by the cross-linking agent, with hydroxylamine in an alkaline medium.

3. The particle of claim 1, wherein the polysaccharide is selected from the group consisting of xanthan gum, guar gum, carobe gum, karaya gum, gum Arabic, an alginate, an agar, a carrageenin, a scleroglucan, a gluco-mannan, a galacto-manan, an arabinogalactan, a pectin, a glycosaminoglycan, a pentosan, a dextran, a chitosan, a chitosan compound, a hydrosoluble starch compound, a hydrodispersible starch derivative, a hydrosoluble cellulose compound, and a hydrodispersible cellulose compound.

4. The particle of claim 3, wherein said starch compound is selected from the group consisting of an alkyl ether of starch, a hydroxyalkyl ether of starch, and a carboxyalkyl ether of starch.

5. The particle of claim 3, wherein said cellulose compound is selected from the group consisting of an alkyl ether of cellulose, a hydroxyalkyl ether of cellulose, and a carboxyalkyl ether of cellulose.

6. The particle of claim 5, wherein said hydroxyalkyl ether of cellulose is a hydroxypropyl cellulose.

7. The particle of claim 5, wherein said carboxyalkyl ether of cellulose is a carboxymethyl cellulose.

8. The particle of claim 1, wherein said protein is a protein of non-regulated use selected from the group consisting of collagen, marine collagen, atelocollagen, marine atelocollagen, a moderate hydrolysate of collagen, a marine collagen hydrolysate, a gelatine, a marine gelatine, and a plant protein.

9. The particle of claim 8, wherein said plant protein is extracted from a leguminous or proteagenous plant selected from the group consisting of lupin (genus Lupinus), soya (genus Glycine), pea (genus Pisum), chick pea (genus Cicer), lucerne (genus Medicago), bean (genus Vicea), lentil (genus Lens), bean (genus Phaseolus), sesame (genus Sesamum), rape (genus Brassica), and sunflower (genus Elientus).

10. The particle of claim 8, wherein said plant protein is extracted from a cereal selected from the group consisting of wheat, maize, barley, malt, and oats.

11. The particle of claim 8, wherein said plant protein is used in the form of a powdery preparation selected from the group consisting of a flour, a concentrate, an isolate, and a liquid preparation.

12. The particle of claim 11, wherein said liquid preparation is a soya milk.

13. The particle of claim 1, which can chelate a metal ion selected from the group consisting of calcium, iron II, iron III, copper I, copper II, chromium, nickel, cobalt, mercury, zinc, silver, aluminium, cadmium, magnesium, lead, arsenic, silicon, selenium, germanium, gadolinium, manganese, a metal ion of a radioactive metal, and a metal ion of a radioactive isotope of a metal.

14. The particle of claim 1 which is loaded with a chelated metal ion, and which is used in a medium to exert a specific role or activity, directly or by release of said chelated metal ions.

15. The particle of claim 14, wherein said metal ion is selected from the group consisting of calcium, iron II, iron III, copper I, copper II, cobalt, zinc, silver, magnesium, silicon, selenium, manganese, and germanium.

16. The particle of claim 1, which is loaded with a metal ion selected from the group consisting of a metal ion of a radioactive metal, a metal ion of a radioactive isotope of a metal, and a metal ion of a paramagnetic metal.

17. The particle of claim 16, wherein said metal ion of a paramagnetic metal is selected from the group consisting of iron, manganese, gadolinium, and their alloys.

18. The particle of claim 16, which becomes detectable by an imaging technique.

19. The particle of claim 18, wherein said imaging technique is selected from the group consisting of scintigraphy, and NMR imaging.

20. A particle selected from a micro-particle and/or a nanoparticle having a surface, which comprises, at least on the surface thereof, a wall composed of a mixture of at least one protein and of at least one polysaccharide which are cross-linked in a reaction medium by interfacial cross-linking with a polyfunctional acylating cross-linking agent which forms at least amide and ester bonds, and optionally anhydride bonds, with amine, hydroxyl or carboxyl functions of the protein and of the polysaccharide, said protein and said polysaccharide being present in said at least cross-linked wall in a relative weight ratio of at least 0.5/0.1 of reaction medium, to provide to said cross-linked wall resistance to degradation by hydroxylamine in an alkaline medium, said particles comprising hydroxamic groups on the surface thereof for chelating metal ions.

21. A particle selected from a micro particle and/or a nanoparticle having a surface, which comprises, at least on the surface thereof, a wall composed of a mixture of at least one protein and of at least one polysaccharide which are cross-linked in a reaction medium by interfacial cross-linking with a polyfunctional acylating cross-linking agent which forms at least amide and ester bonds, and optionally anhydride bonds, with amine, hydroxyl or carboxyl functions of the protein and of the polysaccharide, said protein ranging between 0.5 and 2.5 weight % and said polysaccharide ranging between 0.1 and 10 weight % with respect to the reaction medium, to provide to said cross-linked wall resistance to degradation by hydroxylamine in an alkaline medium, said particles comprising hydroxamic groups on the surface thereof for chelating metal ions.

22. A composition comprising particles of claim 1 which comprise hydroxamic groups on the surface thereof.

23. The composition of claim 22 which is selected from the group consisting of a cosmetic composition, a pharmaceutical composition, an agro-foodstuff composition, and a liquid treatment composition.

24. The composition of claim 23, wherein said liquid is water.

25. A method of preparing particles selected from micro particles and/or nanoparticles having a surface which comprises a first step wherein an interfacial cross-linking is carried out in a reaction medium comprising a mixture of at least one protein and of at least one polysaccharide, with a polyfunctional acylating cross-liking agent to obtain said particles comprising, at least on the surface thereof, amide, ester and optionally anhydride functions, said protein and said polysaccharide being present in said at least cross-linked wall in relative weight proportions sufficient to provide to said cross-linked wall resistance to degradation by hydroxylamine in an alkaline medium, and, in a second step, these cross-linked particles are reacted with hydroxylamine in an alkaline medium to cause rupture at least of ester bonds and optionally anhydride bonds with the linking of hydroxamic groups, which particles are recovered, said particles being there by capable of carrying out the chelation of metal ions.

26. The method of claim 25, wherein for the reaction with hydroxylamine, a relative proportion of hydroxylamine hydrochloride is between 10 and 400 g per kilogram of wet particles to be treated, the pH being adjusted to values between 9 and 13.5 by the addition of a strong base.

27. The method of claim 26, wherein said strong base is sodium hydroxide.

28. The method of claim 26, wherein said pH is adjusted to a value between 9 and 13.5.

29. The method of claim 26, wherein said pH is adjusted to a value between 9.5 and 13.

30. The method of claim 26, wherein said relative proportion of hydroxylamine hydrochloride is between 30 and 200 g/Kg.

31. The method of claim 25, wherein before carrying out the grafting of the hydroxamic group onto the particle, an esterification step is carried out with an alcohol.

32. The method of claim 31, wherein said alcohol is ethanol or benzyl alcohol.

33. A method of preparing particles selected from micro particles and/or nanoparticles having a surface which comprises a first step wherein an interfacial cross-linking is carried out in a reaction medium comprising a mixture of at least one protein and of at least one polysaccharide, with a polyfunctional acylating cross-linking agent to obtain said particles comprising, at least on the surface thereof amide, ester and optionally anhydride functions, said protein and said polysaccharide being present in said at least cross-linked wall in a relative weight ratio of at least 0.5/0.1 of reaction medium, and, in the second step, these cross-linked particles are reacted with hydroxylamine in an alkaline medium to cause a rupture at least of ester bonds and optionally anhydride bonds with the linking of hydroxamic groups, which particles are recovered, said particles being thereby capable of carrying out the chelation of metal ions.

34. A method of preparing particles selected from microparticles and/or nanoparticles having a surface which comprises a first step wherein an interfacial cross-linking is carried out in a reaction medium comprising a mixture of at least one protein and of at least one polysaccharide, with a polyfunctional acylating cross-linking agent to obtain said particles comprising, at least on the surface thereof amide, ester and optionally anhydride functions, said protein ranging between 0.5 and 2.5 weight % and said polysaccharide ranging between 0.1 and 10 weight % with respect to the reaction medium, and, in a second step, these cross-linked particles are reacted with hydroxylamine in an alkaline medium to cause a rupture at least of ester bonds and optionally anhydride bonds with the linking of hydroxamic groups, which particles are recovered, said particles being thereby capable of carrying out the chelation of metal ions.

35. A method of employing or controlled releasing a metal ion in a given medium, comprising the prior preparation of particles selected from microparticles and nanoparticles having a surface of claim 1, wherein hydroxamic groups engaged in chelates with the metal ion that is desired to use or to release into the medium, and placing these particles thus loaded with this chelated metal ion to be used or to be released in contact with the medium in which this use or release must be carried out, for a sufficient period of contact in order to exert a role or a function, or even the release of the metal ion.

36. The method of claim 35 for carrying out a cosmetic treatment, wherein the medium consists of the skin of an animal.

37. The method of claim 36, wherein said animal is a human being.

38. The method of claim 36, wherein said metal to be released is selected from the group consisting of calcium, copper, selenium, zinc, silicon, and germanium.

39. A method of cosmetic treatment of an animal comprising treating said animal with particles selected from microparticles and/or nanoparticles having a surface of claim 1, wherein hydroxamic groups on the surface thereof which are free or engaged in chelates with metal ions on an area of this animal which is sought after, in order to remove these metal ions, or on the contrary, to release these metal ions in said area of the animal.

40. The method of claim 39, wherein said animal is a human being.

41. The method of claim 39 which is a method of protecting materials of the dermis by applying an effective amount of a cosmetic or dermo-pharmaceutical composition containing said particles.

42. The method of claim 39 which is a method of inhibiting enzymatic activities, including collagenase activities, involved in the degradation of the skin support tissues and the intrinsic or photo-inducing ageing of skin tissues by applying an effective amount of said particles for trapping calcium.

43. The method of claim 39 which is a method of inhibiting the activity of certain enzymes involved in the uncontrolled pigmentation of the skin tissues under the action of UV by applying an effective amount of said particles for trapping or releasing copper.

44. The method of claim 39 which is a method of improving the anti-radical defense of the skin while at the same time activating its immune functions by applying an effective amount of said particles which is loaded with a chelated metal ion, and which is used in a medium to exert a specific role or activity, directly or by release of said chelated metal ions.

45. The method of claim 39 which is a method of reducing disorders linked to the accidental presence of nickel or cobalt on the skin by applying an effective amount of said particles.

* * * * *